United States Patent [19]

Axford et al.

[11] Patent Number: 5,157,604
[45] Date of Patent: Oct. 20, 1992

[54] HEART RATE MONITORING SYSTEM FOR PLURAL PERSONS USING RADIO TELEMETRY

[75] Inventors: Ivor R. Axford, Dartmouth; Duane B. Watson, Halifax, both of Canada

[73] Assignee: Her Majesty the Queen in Right of Canada as represented by the Minister of National Defence, Ottawa, Canada

[21] Appl. No.: 297,567

[22] Filed: Jan. 17, 1989

[30] Foreign Application Priority Data

Mar. 7, 1988 [CA] Canada ................................ 560,749

[51] Int. Cl.$^5$ .................. G06F 15/42; A61B 5/0402; A61B 5/0245; H04B 1/00
[52] U.S. Cl. ......................... 364/413.03; 364/413.06; 340/825.08; 455/57.1; 128/903
[58] Field of Search ...................... 364/413.03, 413.06; 128/696, 710, 712, 903; 434/307, 308, 319; 455/57; 340/825.08, 825.54

[56] References Cited

U.S. PATENT DOCUMENTS

| | | | |
|---|---|---|---|
| 3,639,907 | 2/1972 | Greatbatch | 128/903 X |
| 3,646,606 | 2/1972 | Buxton et al. | 128/903 X |
| 3,872,455 | 3/1975 | Fuller et al. | 340/870.05 |
| 4,141,351 | 2/1979 | James et al. | 128/709 X |
| 4,216,462 | 8/1980 | McGrath et al. | 364/413.03 |
| 4,230,989 | 10/1980 | Buehrle | 375/4 |
| 4,347,626 | 8/1982 | Wenzel | 455/57 X |
| 4,384,284 | 5/1983 | Juso et al. | 340/706 |
| 4,477,809 | 10/1984 | Bose | 340/825.54 |
| 4,503,862 | 3/1985 | Baessler | 128/736 |
| 4,518,361 | 5/1985 | Conway | 434/307 |
| 4,566,461 | 1/1986 | Lubbell et al. | 128/668 |
| 4,586,905 | 5/1986 | Groff | 434/307 |
| 4,685,149 | 8/1987 | Smith et al. | 455/56 |
| 4,686,998 | 8/1987 | Robbins | 128/670 |
| 4,709,401 | 11/1987 | Akerberg | 455/57 X |
| 4,802,625 | 2/1989 | Fu et al. | 364/413.03 |

FOREIGN PATENT DOCUMENTS 2420333 11/1979 France ................................ 128/903

OTHER PUBLICATIONS

English Language Translation of FR 2420333.
DeCrosta, T. "Fitness: The pulse monitors you love to hate", Exersentry Heart Rate Monitor, *Bicycling*, Apr. 30, 1982.
Exersentry TM brochure, Respironics Inc., date unknown.

*Primary Examiner*—Clark A. Jablon
*Assistant Examiner*—Laura Brutman
*Attorney, Agent, or Firm*—William R. Hinds

[57] ABSTRACT

An apparatus for simultaneously monitoring the heart rate of each of a plurality of subjects comprises a main circuit for transmitting a predetermined signal of predetermined frequency and duration and at predetermined time intervals to cause each of a plurality of remote subcircuits to transmit subcircuit identity data and heart rate data in predetermined timed sequence, a receiver for receiving remote subcircuit transmissions and producing an output representative of the heart rate of a subject and a plurality of remote subcircuits, each remote subciruit having a pulse monitoring device adapted to be secured to a subject for detecting and producing an output in response to a heart beat, and a detector for detecting the pulse monitoring device output and determining the number of the outputs which occur within a predetermined time interval, and being responsive to the main circuit predetermined signal for transmitting to the main circuit a signal representative of subcircuit identity data and the number of the detected heart beats.

30 Claims, 19 Drawing Sheets

```
**************************************

HEART BEAT MONITOR SYSTEM
```

FIG. 7a

```
************ IMPORTANT OPERATOR DATA ************

OPERATOR:--------    RANK:----  DATE:01/30/87   TIME: 14:24:09

TAB-ADVANCE TO NEXT AREA    RETURN-WHEN ALL ENTRIES ARE CORRECT
```

FIG. 7b

```
**************** PARTICIPANT DATA ****************

AGE GROUP: 15-19       NUMBER OF PARTICIPANTS: 1        SEX:MALES
      SPACE-TO CHANGE AGE GROUP, # OF PARTICIPANTS OR SEX,
                       THEN PUSH RETURN
```

FIG. 7c

```
* * * * * * * * * * INDIVIDUAL PARTICIPANT DATA * * * * * * * * * *
   PARTICIPANT #    SURNAME          RANK    AGE    WEIGHT(kg)
        1           --------,-       ----    --     ---
   TAB-ADVANCE TO NEXT AREA    RETURN-ADVANCE TO NEXT PARTICIPANT
      * * * NOTE: AGE AND WEIGHT MUST BE CORRECT TO PROCEED * * *
```

FIG. 7d

```
* * * * * * * * * * INDIVIDUAL PARTICIPANT DATA * * * * * * * * * *
   PARTICIPANT #    NAME             RANK    AGE    WEIGHT(kg)
        1           JONES----,D      ENGN    18     70-
        2           --------,-       ----    --     ---
        3           --------,-       ----    --     ---
        4           --------,-       ----    --     ---
   TYPE 'SPACE' TO SEE NEXT GROUP, 'C' TO MAKE CORRECTION, OR 'P' TO PROCEED
```

FIG. 7e

```
* * * * * * * * * * DATA CORRECTION AREA * * * * * * * * * * * *
   PARTICIPANT #    NAME             RANK    AGE    WEIGHT(kg)
        1           JONES----,D      ENGN    18     70-
   TAB-ADVANCE TO NEXT AREA    RETURN-ADVANCE TO NEXT PARTICIPANT
      * * * NOTE: AGE AND WEIGHT MUST BE CORRECT TO PROCEED * * *
```

FIG. 7f

TURN ON PRINTER POWER SWITCH. IS ALL DATA CORRECT? (Y/N)

FIG. 7g

PLEASE INSERT THE MUSIC MICRO-CASSETTE-
MALE SIDE UP-INTO THE DECK.

PRESS 'RETURN' KEY WHEN READY TO PROCEED

FIG. 7h

READING SONG INDEX-----PLEASE WAIT

USE THIS TIME TO PREPARE THE PARTICIPANTS

FIG. 7i

```
* * * * * * * * * * * * * TEST RESULTS * * * * * * * * * * * * * *
--TIME--            -------- PARTICIPANT # ----------
             1  2  3  4  5  6  7  8  9  10 11 12 13 14 15 16

PUSH 'D' TO START OR 'F' TO STOP DEMO MUSIC OR 'RETURN' TO START TEST.

#LB=    TEST#1 THRES=174 bpm    BUZZ=ON    PUSH 'U'- UNIT STATUS
```

FIG. 7j

```
* * * * * * * * * * * * * UNIT STATUS * * * * * * * * * * * * * *
             ------------- UNIT # ----------
             1  2  3  4  5  6  7  8  9  10 11 12 13 14 15 16
HB OR STAT-70 OFF OFF OFF OFF OFF OFF OFF OFF OFF OFF OFF OFF OFF OFF OFF
BATTERY   -OK

MAIN BAT = 13.25 V        PUSH 'E'- TO EXIT UNIT STATUS
```

FIG. 7k

```
* * * * * * * * * * * * * TEST RESULTS * * * * * * * * * * * * * *
--TIME--            -------- PARTICIPANT # ----------
             1  2  3  4  5  6  7  8  9  10 11 12 13 14 15 16

0:0       80  0  0  0  0  0  0  0  0  0  0  0  0  0  0  0

#LB=0 TEST#1 THRES 174 bpm    BUZZ=ON    PUSH 'A' TO ABORT TEST
```

FIG. 7l

```
* * * * * * * *PLEASE PICK WHAT YOU WANT TO DO * * * * * * * *
         'S'-- START OVER WITH SAME PARTICIPANTS
         'N'-- NEW TEST WITH NEW PARTICIPANTS
         'O'-- POWER OFF
         'U'-- UNIT STATUS
         'C'-- CALC VO2 MAX
```

FIG. 7m

HEART RATE MONITORING SYSTEM FOR PLURAL PERSONS USING RADIO TELEMETRY

The present invention relates to an apparatus for simultaneously monitoring the heart rate of a plurality of subjects while the subjects are undergoing physical exertion tests and is an improvement over the invention disclosed and claimed in the present Assignee's copending Canadian Patent Application Ser. No. 518,682 filed Sep. 19, 1986 for MULTIPLE HEART RATE MONITOR.

BACKGROUND OF THE INVENTION

Canadian armed forces personnel are required to undergo an annual health examination involving the use of a test known as the "EXPRES TEST". As is generally well known, the test involves having a subject repeatedly ascend and descend a number of steps for a predetermined period of time and recording the subject's heart rate count at the end of that period. The test is usually repeated three or four times in succession. It is necessary to continuously monitor the subject's heart rate count during the course of the test to ensure that the count does not exceed a predetermined safe count for the age category of the subject and, thus, that the subject is not over-stressed.

Heretofore, the EXPRES TEST has been conducted on an individual basis, i.e. one physical education and recreation instructor (PERI) evaluating one person at a time. When conducted on a one on one bases, that the testing and evaluation of all armed forces personnel is time consuming and expensive. There is a demonstrated need therefore for a reliable system which will allow one physical education and recreation instructor to simultaneously oversee for testing of several persons so as to expedite and reduce the cost of conducting the EXPRES TESTS.

SUMMARY OF THE INVENTION

The present invention seeks to provide an apparatus which will allow simultaneous evaluation of several subjects and, thus, allow more efficient and effective use of supervisory personnel and resources.

In accordance with one aspect of the present invention, there is provided an apparatus for simultaneously monitoring the heart rate of each of a plurality of subjects, comprising a main circuit having means for transmitting a predetermined signal of predetermined frequency and duration and at predetermined time intervals to cause each of a plurality of remote subcircuits to transmit subcircuit identity data and heart rate data in predetermined timed sequence, means for receiving remote subcircuit transmissions and producing an output representative of the heart rate of a subject and a plurality of remote subcircuits, each remote subcircuit having pulse monitoring means adapted to be secured to a subject for detecting and producing an output in response to a heart beat, means for detecting the pulse monitoring means output and determining the number of the outputs which occur within a predetermined time interval, and means responsive to the main circuit predetermined signal for transmitting to the main circuit a signal representative of subcircuit identity data and the number of the detected heart beats.

In accordance with another aspect of the present invention, there is provided a kit for use in simultaneously monitoring the heart rate of each of a plurality of subjects, the kit comprising a carrying case, a microcomputer, including a video display screen and keyboard, mounted in the case, a printer mounted in the case and adapted to be connected to the computer, a tape cassette player mounted in the case and adapted to be connected to and controlled by the computer, audio speaker means removably mounted in the case and adapted to be connected to the tape player, primary circuit means mounted within the case and electrically connected to the microcomputer and including transmitter and receiver means for receiving and transmitting radio signals, encoding circuitry for generating and transmitting radio signals at predetermined intervals and digital decoding circuitry for decoding received digital signals and imputing decoded signals into the microcomputer, and a plurality of participant units adapted to be stored in the case and being removable therefrom for attachment to a test participant, each the participant unit being adapted to be electrically connected to a participant pulse monitoring device and having secondary circuit means including circuit means adapted to receive the output of the pulse monitoring device for detecting and storing the number of participant heart beats occurring within a predetermined time interval and for encoding data for transmission to the primary circuit means, and transmitter and receiver means for receiving transmission by the primary circuit means and transmitting encoded participant data thereto.

BRIEF DESCRIPTION OF THE DRAWINGS

These and other features of the invention will become more apparent from the following description in which reference is made to the appended drawings wherein:

FIGS. 7a–7m illustrate a number of data entry and selection screens output to the computer display terminal.

DETAILED DESCRIPTION OF PREFERRED EMBODIMENT

Figure 1:
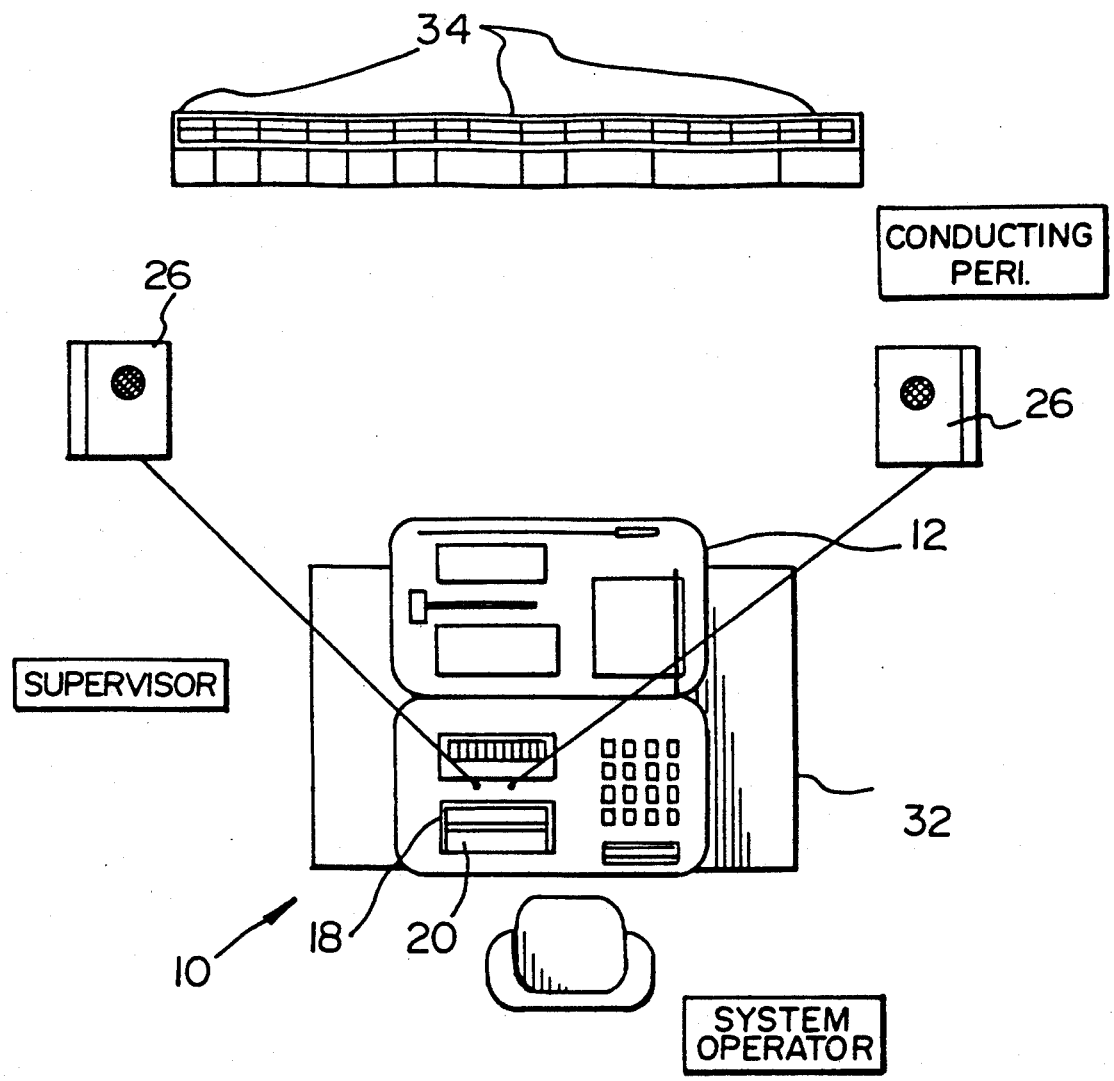
FIG. 1 is a schematic plan view of a test site organization.
Figure 2:
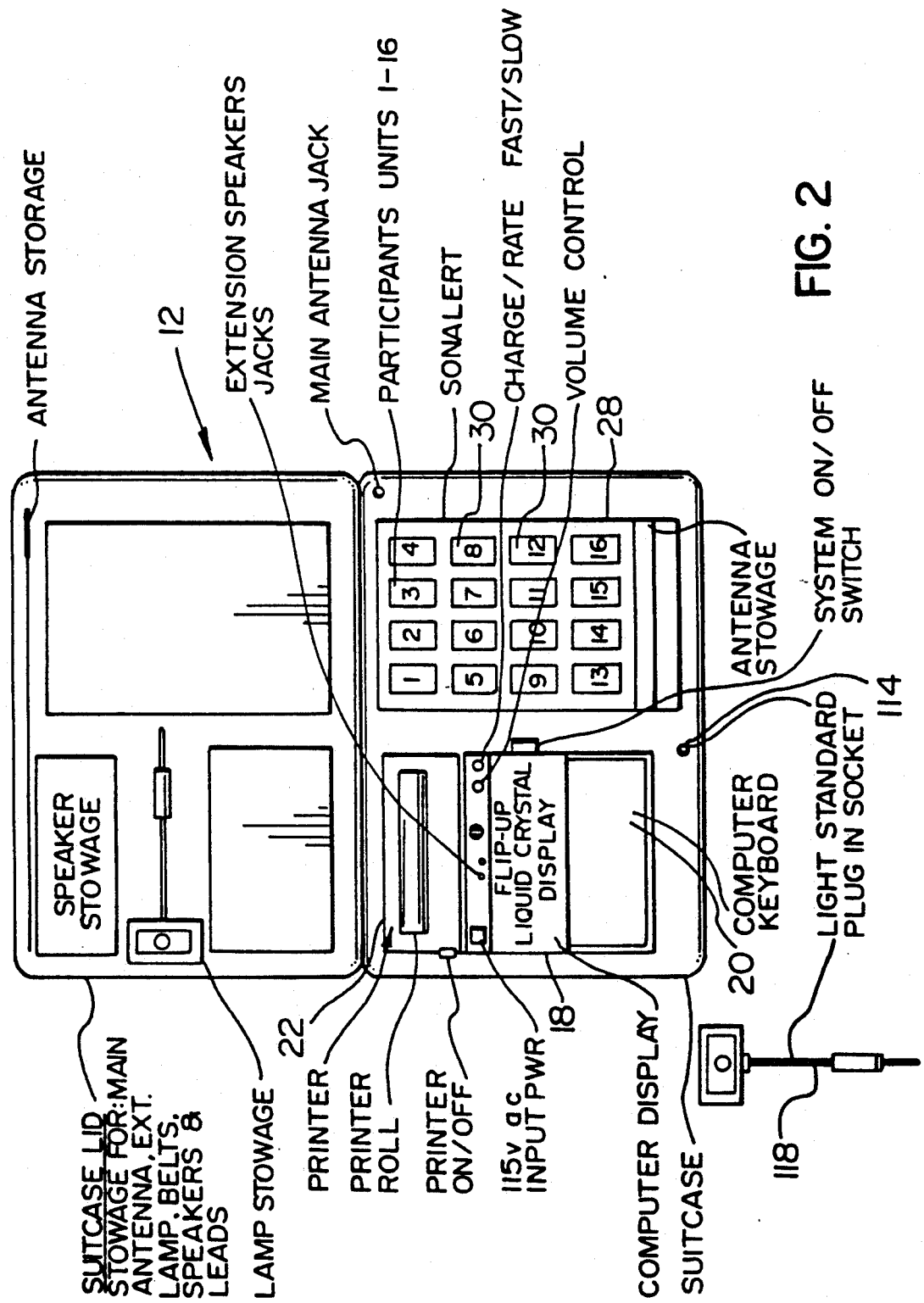
FIG. 2 is a schematic top plan view of an opened carrying case illustrating a computer display and keyboard, printer, remote subcircuit storage compartments, speaker and other such peripheral equipment and in which the computer and main circuit board are housed according to a preferred embodiment of the present invention.

FIG. 1 illustrates the operational layout of the Heart Beat Monitoring system, generally designated by reference numeral 10, of the present invention. The system includes, as shown in FIG. 1 and 2, a carrying case 12 which houses a main circuit board 14 and other associated circuit boards described later, a microcomputer 16 known by the trademark EPSON PX-8, and an associated liquid crystal display terminal 18 and keyboard 20, a thermal printer 22, a tape cassette player (not shown) which is an integral part of the EPSON PX-8 computer, a pair of speakers 26,26, a charging rack 28 adapted to removably hold a plurality (16 are shown) of participant units 30 and other components such as antennae and a lamp fixture for use with the display terminal.

As shown, carrying case 12 is placed on a table 32 and opened. The speakers are removed from their respective storage compartments and placed adjacent the opposite ends of test steps 34 or at any other suitable location and their leads are connected to tape cassette player housed in the carrying case.

Each participant or subject is provided with one of the aforementioned participant units 30 which are equipped with a belt. Each unit includes a main circuit board 40 and a transceiver circuit board 42 (see FIG. 3) and is adapted to be connected to a pulse monitoring device (not shown) which, in turn, is adapted to be secured to the subject in known manner. Each unit further includes an internal rechargeable battery 44 which can be recharged when stored in charging rack 28 in the carrying case and the system is connected to 117 VAC.

The microcomputer contains BASIC programs and a multi-level machine language program that allows the internal hardware of the computer to form an integral part of the electronic circuitry of the heart beat monitoring system of the present invention. The computer monitors all system functions and allows the operator to enter participant data and observe participant heart rates while the EXPRES TESTS are in progress and issues an audible alarm in the event that any heart rate exceeds a predetermined threshold level so as to allow the operator to remove the participant from the test if necessary. The music necessary for the step test is contained on microcassettes that can be played under computer control during each test.

As explained more fully later, at five second intervals during the course of the tests, the main circuit board 14 transmits a signal of predetermined frequency and duration to all of the remote participant units. This signal causes the units to transmit back, in predetermined sequence, remote unit identity data, heart rate data and battery condition data.

Figure 3A:
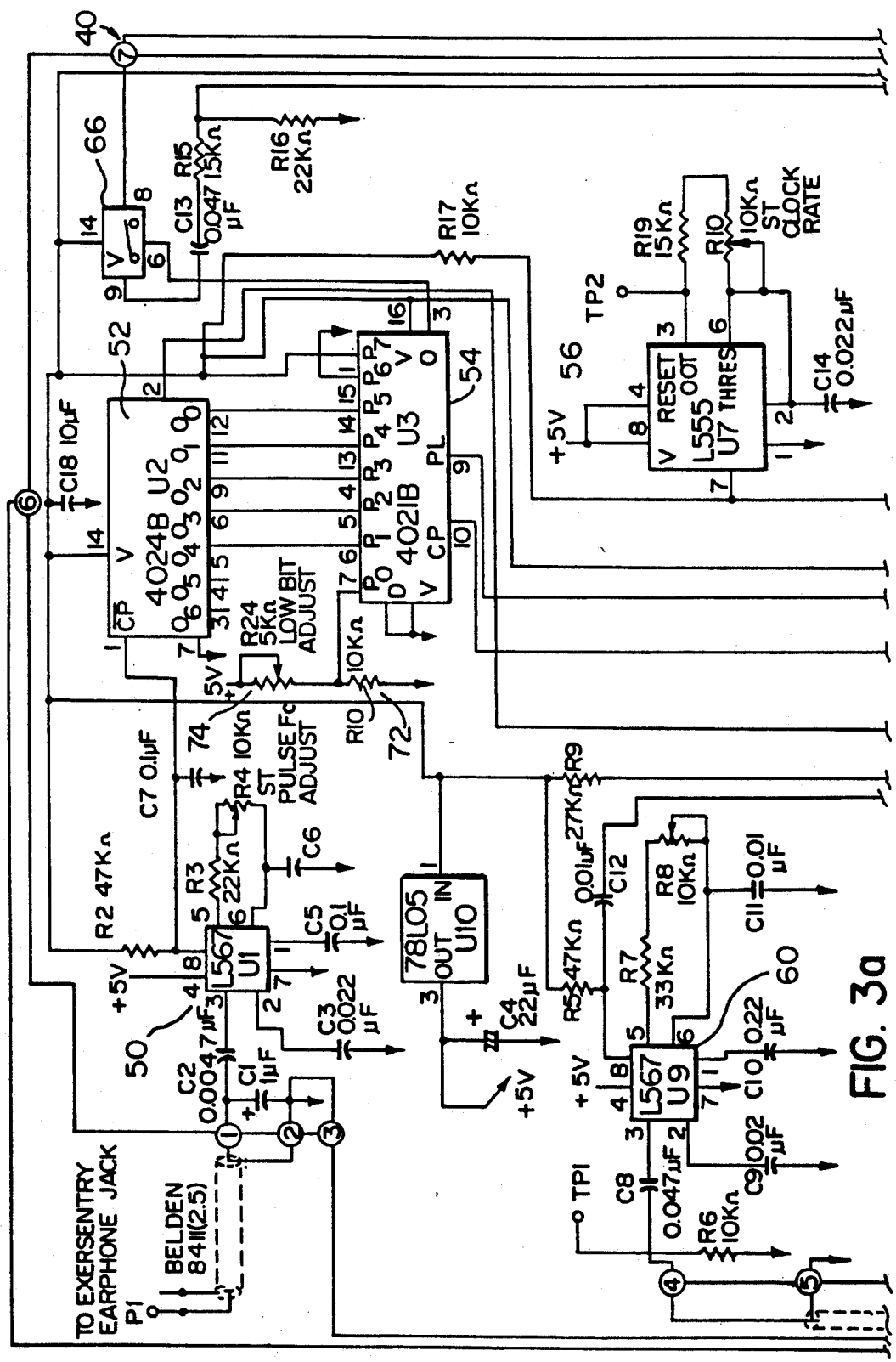
FIGS. 3a–c are electrical circuit diagrams illustrating a remote subcircuit including a main circuit board and a radio transceiver circuit board according to a preferred embodiment of the present invention.
Figure 3B:
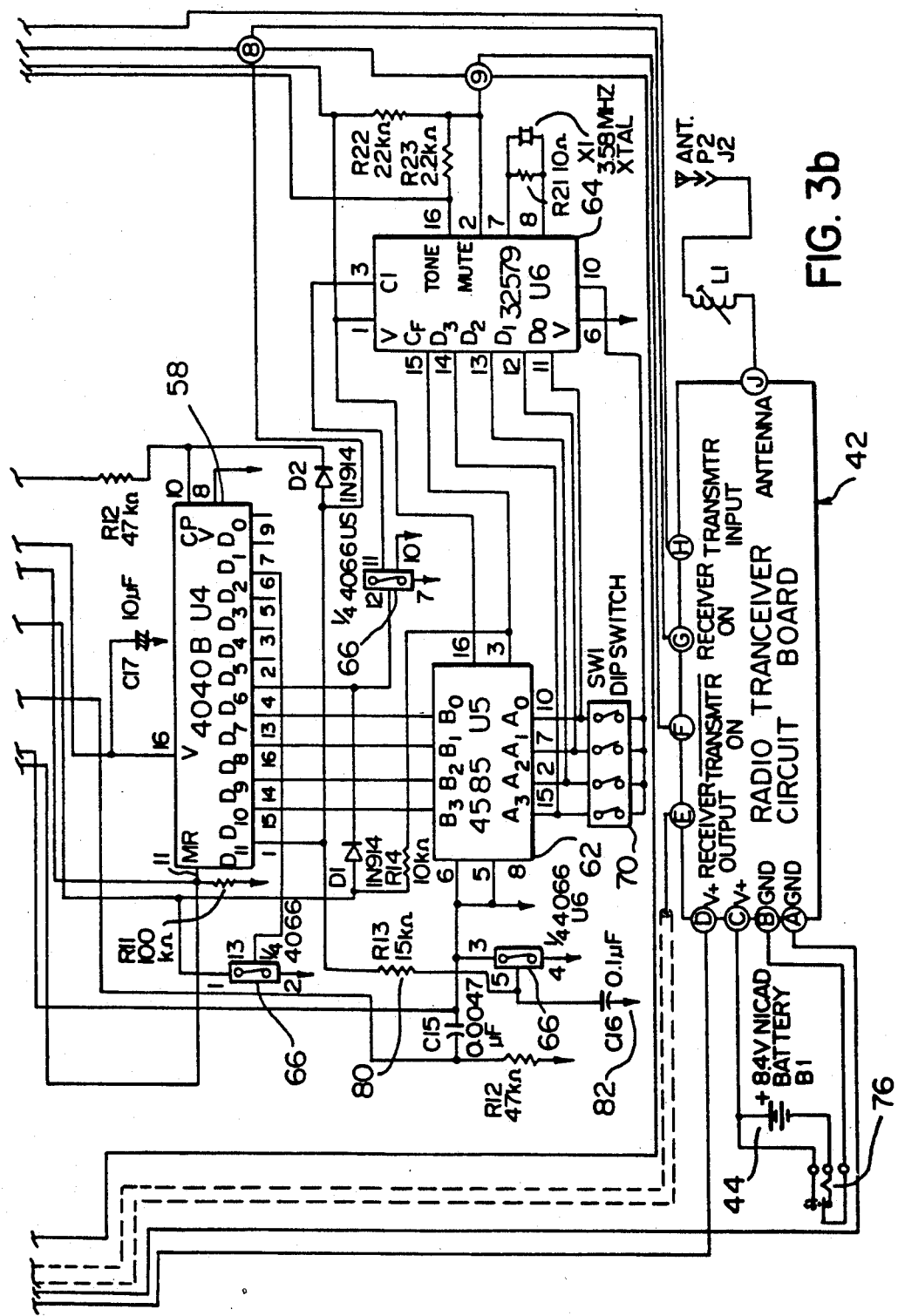
Figure 3C:
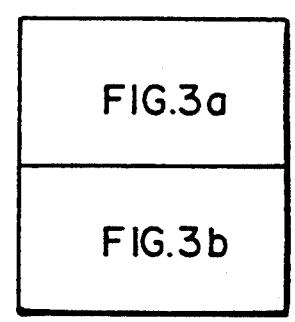
Figure 5D:
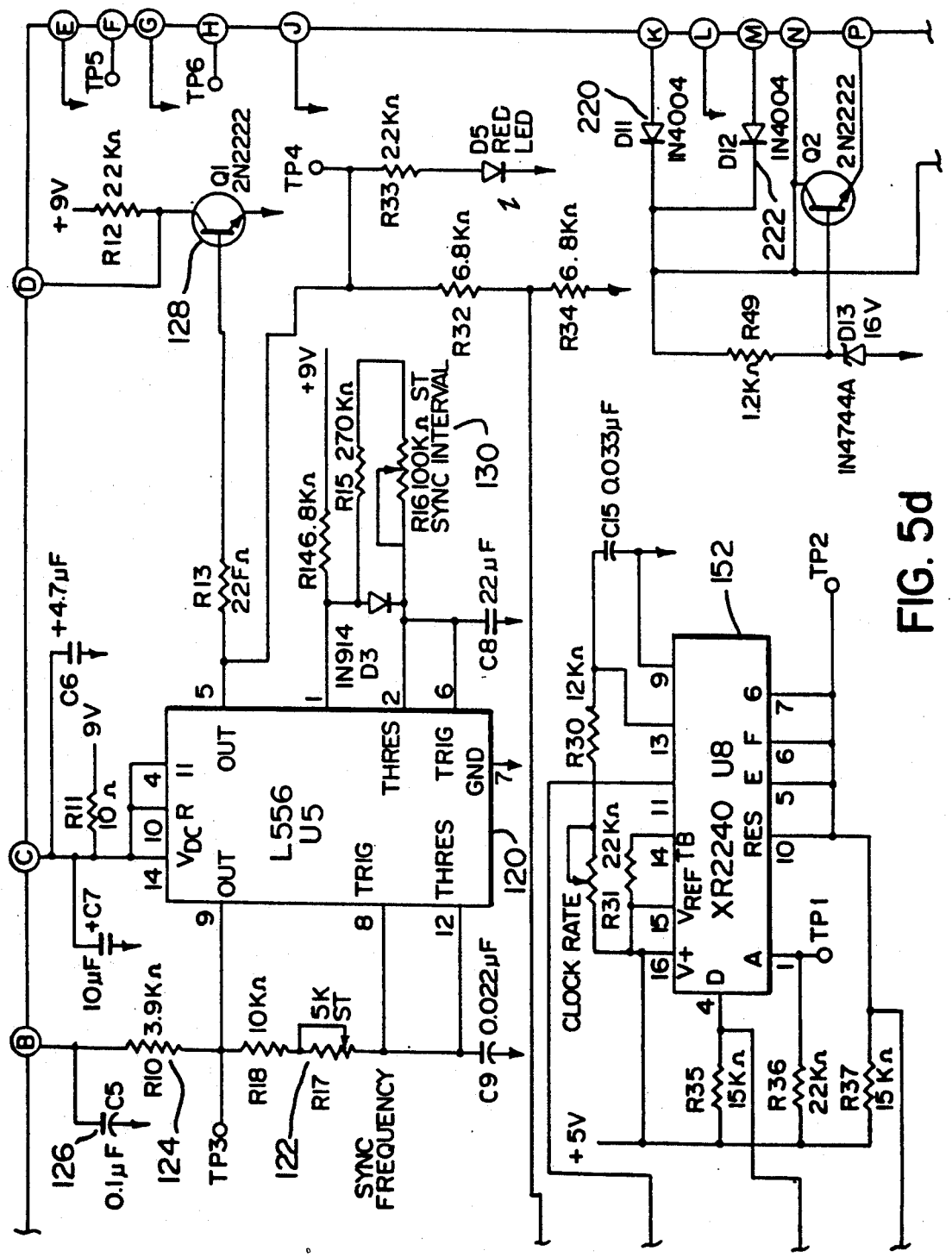
Figure 5E:
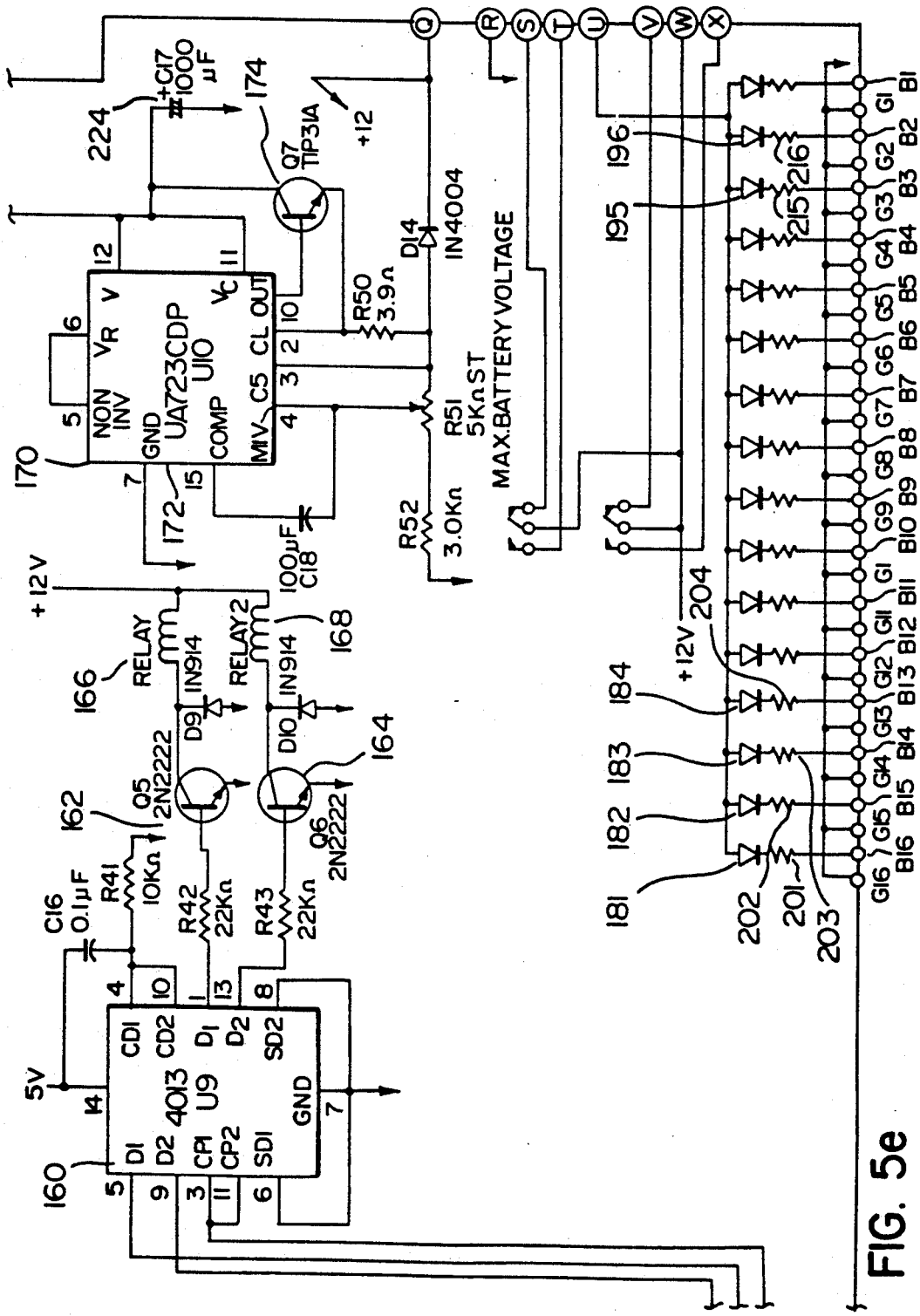

Participant units 30 will now be described with reference to FIG. 3 of the drawings. As mentioned previously, each participant unit 30 includes a main circuit board 40 and a radio transceiver circuit board 42. The transceiver circuit board is provided with a number of connection points referenced later and employs a standard FM antenna for transmitting and receiving FM signals to and from the main circuit board of the main unit. Otherwise, transceiver 42 employs conventional circuitry and, accordingly, will not be described in detail herein.

The main circuit board 40 is adapted to be connected to the earphone jack of a pulse monitoring device (not shown) known by the trademark EXERSENTRY. This device is adapted to be secured to a participant in known manner for detecting the peak in a subject's EKG waveform and, in response to each detected peak, produce a tone burst at its earphone output at a frequency of 1666 hz for a duration of 100 ms.

Main circuit board 40 contains the logic circuitry for counting heartbeats and synchronizing data transmission and includes the following major components: a first L567 TONE DECODER 50, a 4024 7-STAGE RIPPLE COUNTER 52, a 4021 8-STAGE STATIC SHIFT REGISTER 54, an L555 OSCILLATOR 56, a 4040 12-STAGE BINARY COUNTER 58, a second L567 TONE DECODER 60, a 4585 4 BIT MAGNITUDE DETECTOR 62, a DUAL TONE MULTI-FREQUENCY (DTMF) GENERATOR 64, a CMOS SWITCH 66, a 5 VOLT VOLTAGE REGULATOR 68, and a DIP SWITCH 70.

TONE DECODER 50 is adapted to receive the output of the pulse monitoring device and drop its output from a high level to a low level when it detects the 1666 hz tone burst. Its output returns to a high level when the tone burst ends. Its output is connected to the pulse input of RIPPLE COUNTER 52. Each low level output of the TONE DECODER increments the binary output of the RIPPLE COUNTER by one to a maximum of 31 counts. Five of the seven outputs of the RIPPLE COUNTER are connected to the five parallel inputs of SHIFT REGISTER 54. A voltage divider consisting of resistor 72 and adjustable resistor 74 connect a 5 volt power supply to the $P_0$ pin of the SHIFT REGISTER.

Resistor 74 is adjusted to provide approximately four volts at Pin 7 of the SHIFT REGISTER. The power supply is the 8.4 V rechargeable battery 44. When the battery voltage falls below 7 volts, the voltage at the $P_0$ input of the SHIFT REGISTER is greater than the high input threshold voltage for CMOS logic and the input changes from a logic 0 indicating a charged battery condition to a logic 1 to indicating a low battery condition.

When the participant unit is removed from the charging rack in the carrying case, battery power is applied to the circuitry by a switch 76 controlled by charging jack JK1. This causes OSCILLATOR 56 to generate clock pulses at a rate of 1067 pulses per second which are applied to the clock input of BINARY COUNTER 58. When output $O_{11}$ of the BINARY COUNTER goes to 8.4 V, the clock input is forced high causing the BINARY COUNTER 58 to stop counting until it receives a SYNC PULSE signal from second TONE DECODER 60 which is connected to the receiver input.

Output $O_{11}$ of the BINARY COUNTER is connected to the RECEIVER ON input "G" of transceiver circuit 42. The receiver thereof is turned ON by a high level output from $O_{11}$ so as to monitor transmissions from main circuit 14.

When the main circuit transmits a 120 ms burst of a 2600 hz SYNC PULSE signal, TONE DECODER 60 locks onto this signal and sets its output low. The trailing rising edge of the 2600 hz SYNC PULSE signal causes the BINARY COUNTER to be reset and the binary heart beat count in RIPPLE COUNTER 52 to be latched into SHIFT REGISTER 54. As the BINARY COUNTER resets, its output $O_{11}$ goes low which turns the receiver circuitry OFF, to conserve power and reject other transmissions, the RIPPLE COUNTER is reset and the BINARY COUNTER's clock is enabled. Outputs $O_7$ to $O_{10}$ of the BINARY COUNTER are used to determine the elapsed time between SYNC PULSE reception and participant unit transmission as explained hereinbelow.

Output $O_2$ of the BINARY COUNTER provides the clock input for the SHIFT REGISTER and therefore determines the baud rate of the digital transmission of the SHIFT REGISTER. Output $O_6$ of the BINARY COUNTER is connected to the C1 input of DTMF GENERATOR 64 through CMOS SWITCH 66 and the value of this output determines whether the transmitted data is a Dual Tone MultiFrequency (DTMF) code or an 8-bit serial type. A logic 1 is represented by the presence of a high frequency signal while a logic 0 is represented by the absence of a high frequency signal. It is to be noted at this point that the $O_6$ output of the BINARY COUNTER is low during the first half of data transmission and high for the second half of data transmission. This means that a high frequency signal will be present during the first half of transmission and serial data, the output of the SHIFT REGISTER, will be present during the during the second half of data transmission.

DIP SWITCH 70 sets the identity code for each participant unit. Its four output pins are connected in parallel to four input pins of MAGNITUDE COMPARATOR 62 and in series to an input of DTMF GENERATOR 64. COMPARATOR 62 sets its equality output equal to its equality input whenever the count of BINARY COUNTER 58 equals the output of the DIP SWITCH. For ID codes 1 to 15, the equality input of the COMPARATOR is set to a logic 1 immediately after the ID codes match. When the ID code is 0, a short delay is generated by resistor 80 and capacitor 82 to ensure proper latching of GENERATOR 64.

When the equality output of the COMPARATOR goes high, the chip enable (CE) input of the DTMF GENERATOR goes high and the binary ID code of the DIP SWITCH is latched into the DTMF GENERATOR. Since the $O_6$ output of the BINARY COUNTER is low during the first half of data transmission, the C1 input of the DTMF GENERATOR will be high and a DTMF tone will be generated at the tone output pin of the DTMF GENERATOR. The mute output pin of the DTMF GENERATOR is connected to the TRANSMITTER ON terminal "H" of the transceiver. As long as the CE input of the DTMF GENERATOR is high, the mute output will be low and the transmitter will be turned ON. The tone output is fed through CMOS SWITCH 66 and into the transmitter input. At this stage, the $O_7$ output of the SHIFT REGISTER is a high logic level since $P_7$ is tied to the 8.4 V source and the SHIFT REGISTER has not been shifted. The $O_7$ input enables the gate of the CMOS SWITCH and the DTMF tone is fed to the transmitter and is radiated.

After 60 ms, output pin $O_6$ of the BINARY COUNTER goes high which enables the clock input to the SHIFT REGISTER and sets the C1 input of the DTMF GENERATOR to a logic 0. The tone output of the DTMF GENERATOR will now the high frequency group (1209-1633 hz) of the DTMF tone pairs which is gated ON or OFF depending on the $O_7$ output of the SHIFT REGISTER. The serial data from the SHIFT REGISTER is now transmitted and consists of a zero start bit followed by five bits representing the heart beat (least significant bit first), a batter condition bit and a zero stop bit as the eighth and last bit.

The transmission time for each participant unit is 120 ms for a total of 1.92 seconds for all 16 units. Voltage regulator 68 provides a regulated 5 volts for the voltage sensitive logic which helps reduce device dissipation and increases battery life.

When the ID codes no longer match, the CE input of the DTMF GENERATOR goes low, its mute output goes high and the transmitter is thereby turned OFF. The unit then waits until another SYNC PULSE signal is detected which will cause the process to repeat. In the meantime, TONE DECODER 50 and RIPPLE COUNTER 52 will continue to detect and count tone bursts in preparation for the next transmission.

Figure 4A:
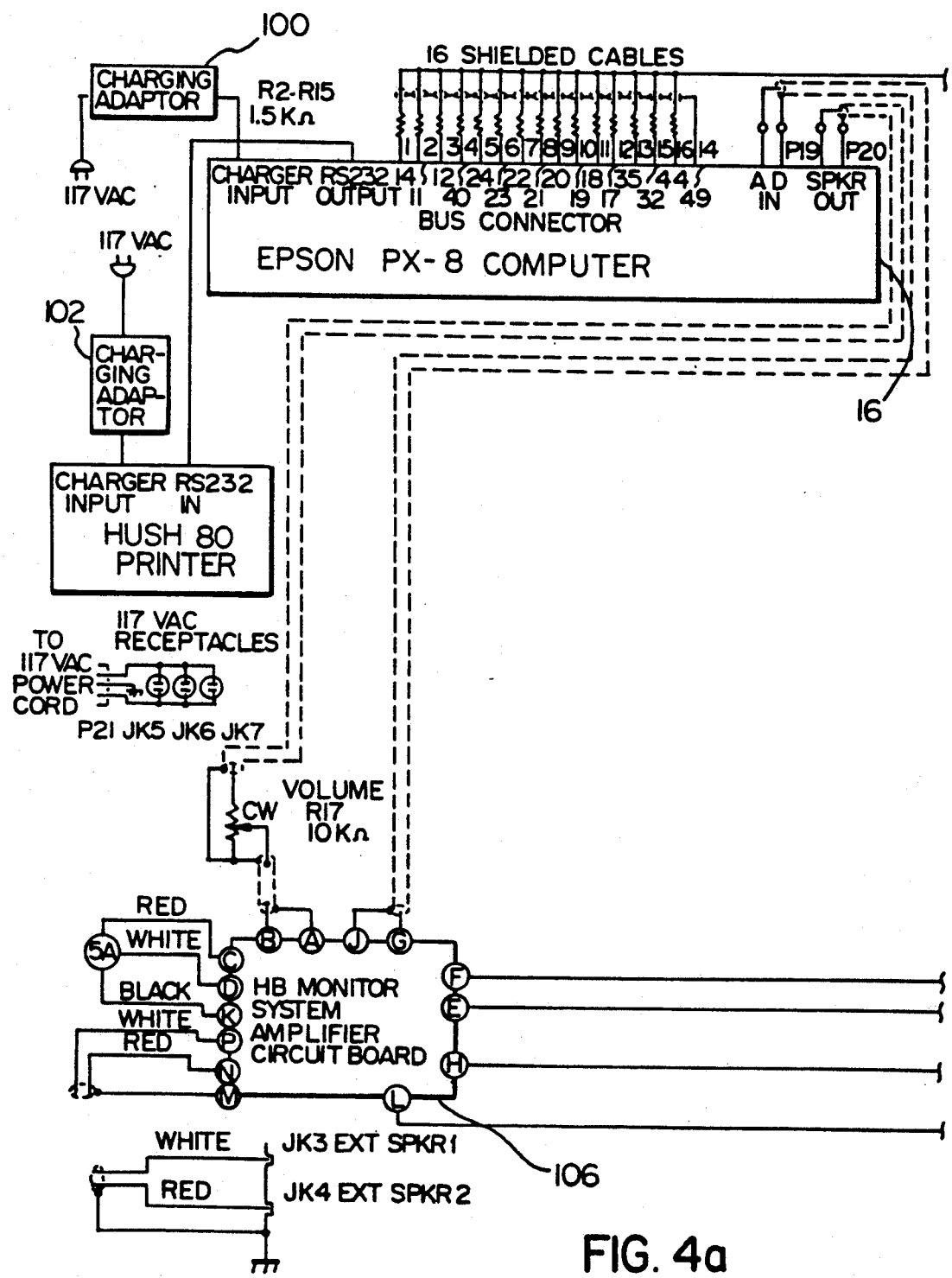
FIGS. 4a–c are elementary electrical circuit diagrams illustrating the main components of the Heart Beat Monitor according to a preferred embodiment of the present invention.
Figures 4B, 4C:
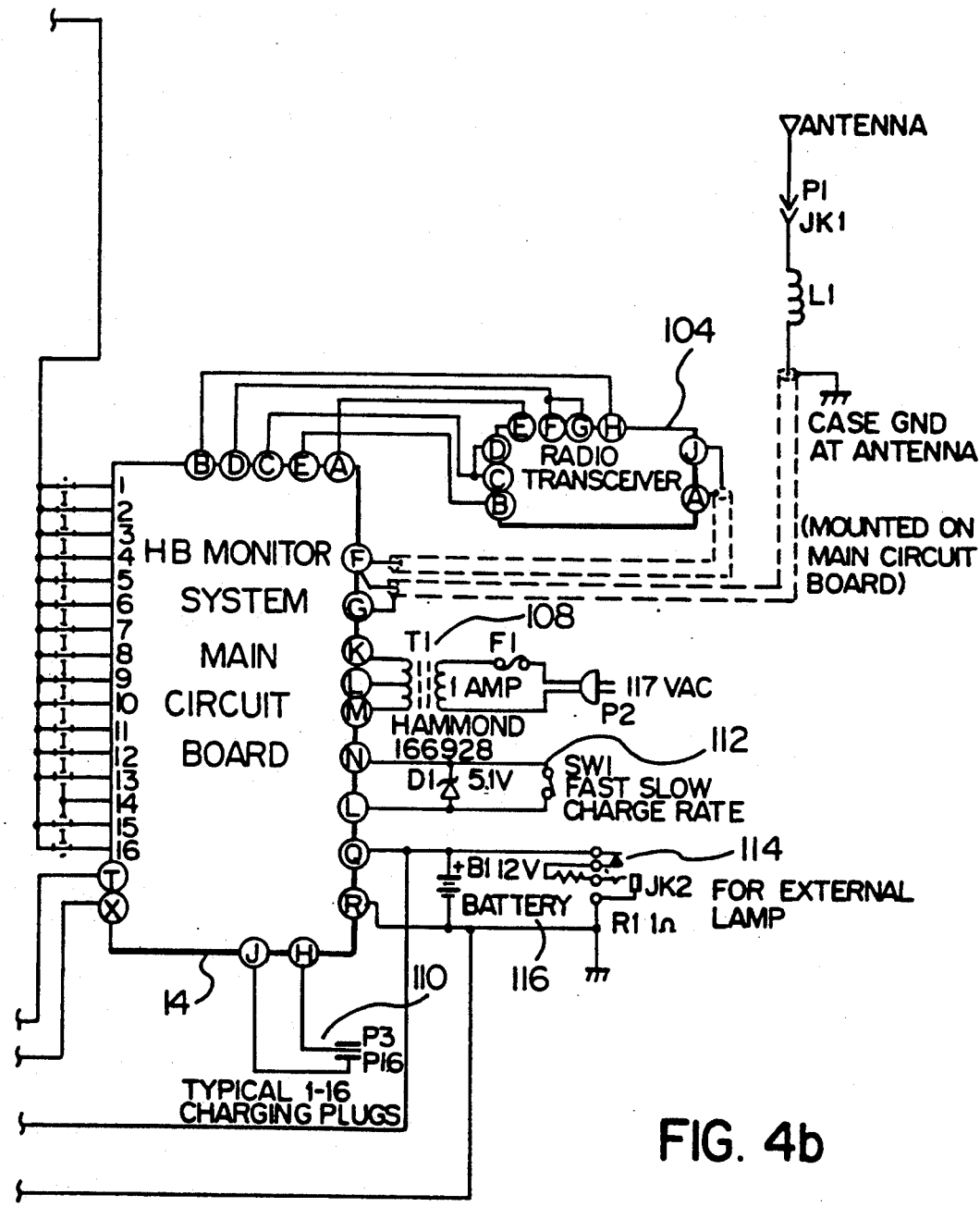
Figure 5A:
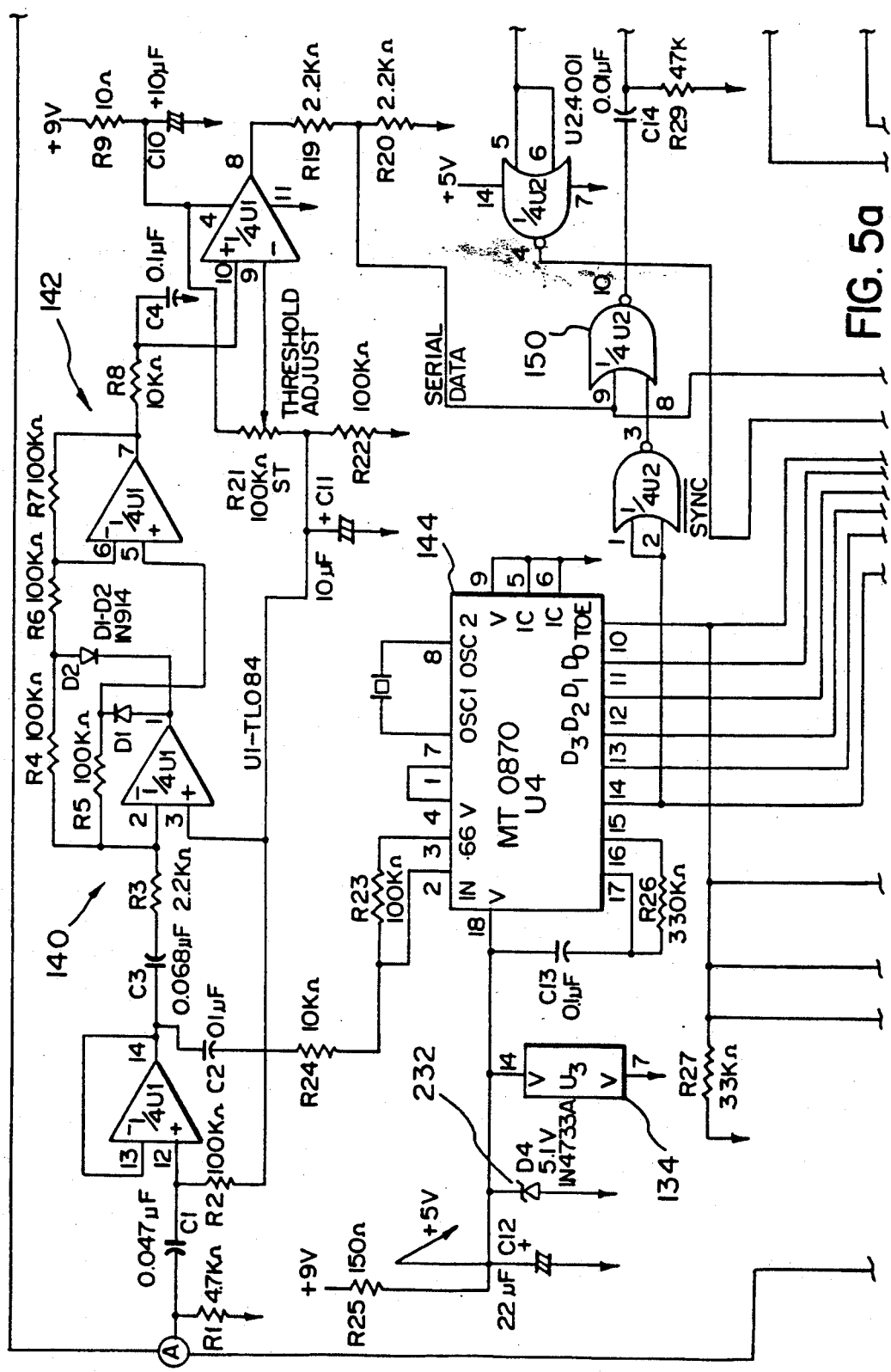
FIGS. 5a–f are electrical circuit diagrams illustrating the Heart Beat Monitor main circuit board according to a preferred embodiment of the present invention.
Figure 5B:
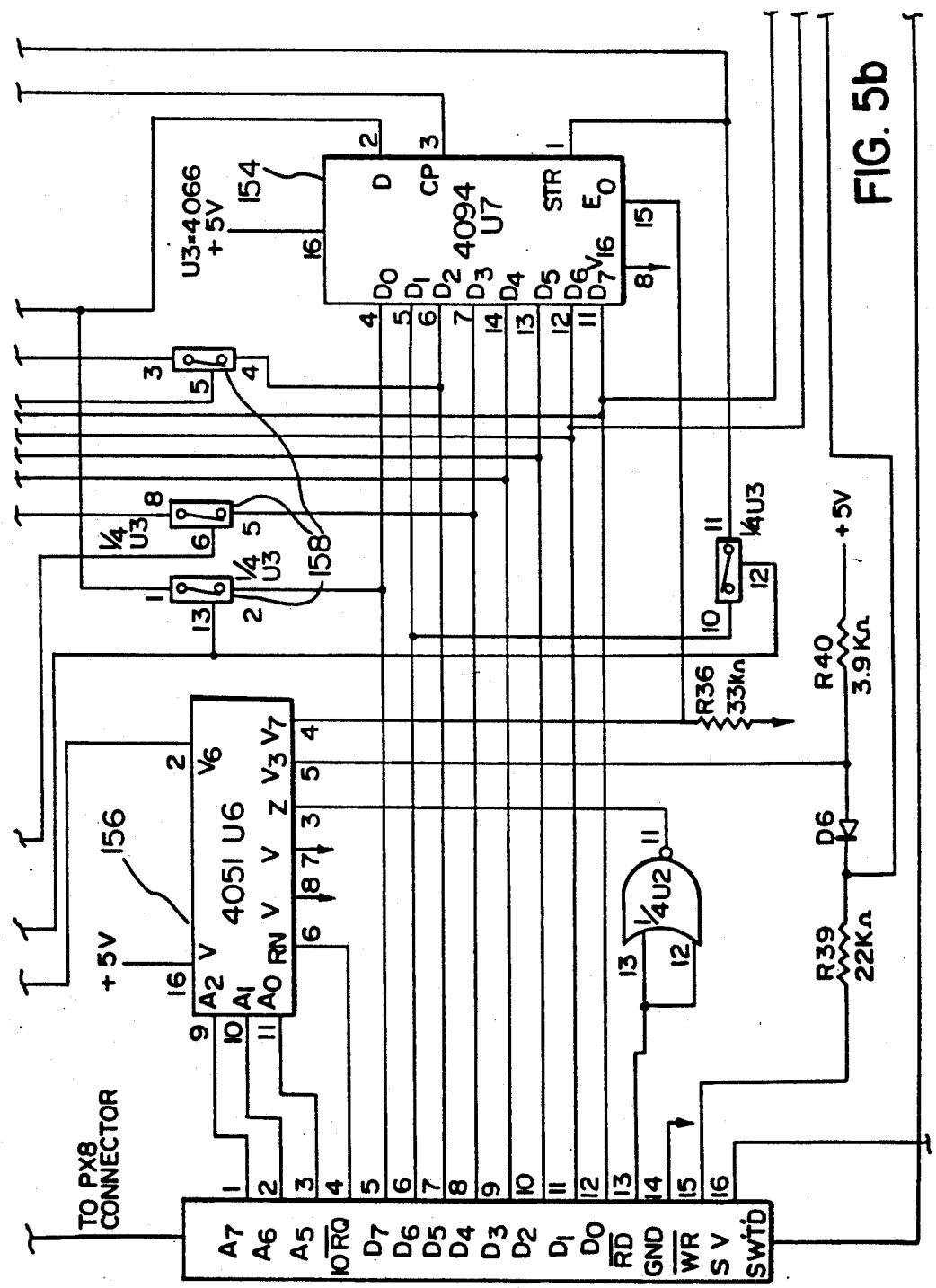
Figure 5C:
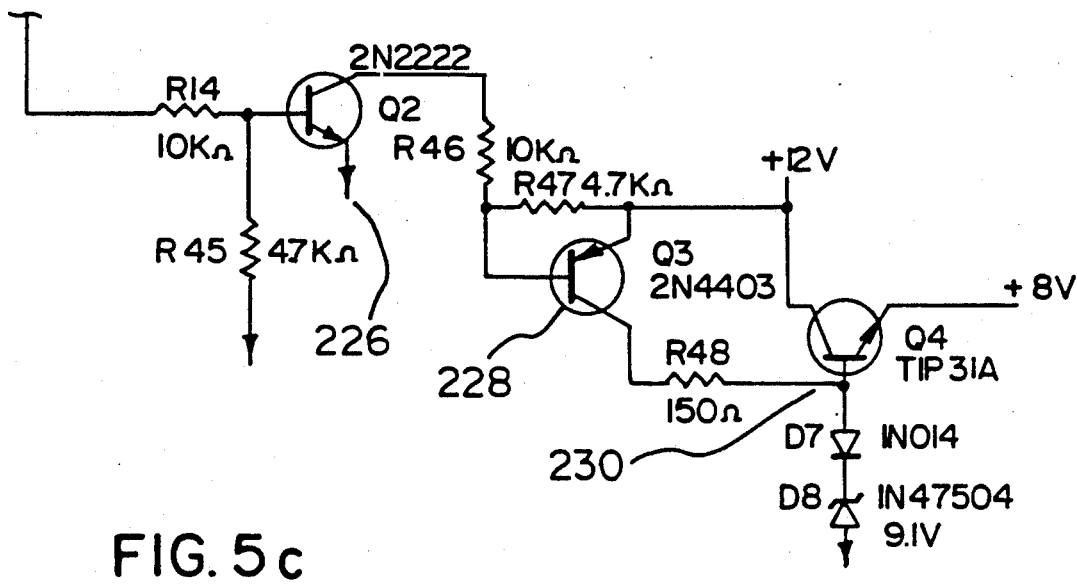
Figure 5F:
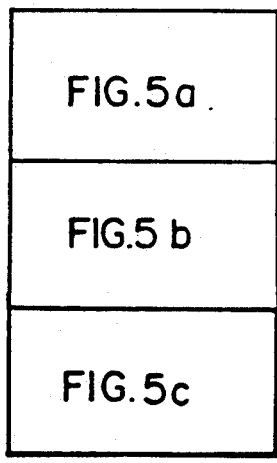

With reference to FIG. 4, the main unit includes aforementioned main circuit board 14, EPSON PX-8 microcomputer 16 having a charging adaptor 100, printer 22 having charging adaptor 102, a radio transceiver circuit board 104 and an amplifier circuit board 106. The transceiver circuit board 104 is provided with a number of connection points referenced later and employs a standard FM antenna for transmitting and receiving FM signals to and from the participant unit transceiver circuit boards. Otherwise, as with transceivers 42, board 104 employs conventional circuitry and, accordingly, will not be described in detail herein.

The main circuit board is adapted to be connected to 117 VAC through a transformer 108. 16 charging plugs 110 are connected the main circuit board and are adapted to be connected to mating plugs (not shown) on the participant circuit boards when the participant units are placed the charging rack. A fast/slow switch 112 is provided for varying the charging rate of the participant board rechargeable batteries.

An external lamp jack 114 connected in parallel with a battery 116 is connected to the main board. An external lamp 118 may be desirable under some conditions to enhance the display of the terminal.

The main board includes radio synchronizing and decoding circuitry which includes an L556 DUAL TIMER 120. One half of this timer generates the 2600 hz SYNC PULSE square wave signal which is adjustable using resistor 122. The signal is low pass filtered by resistor 124 and capacitor 126 and fed to the FM transmitter output. The other half of TIMER 120 controls a transistor 128 which, when ON, activates the transmitter which, in turn, radiates the 2600 hz SYNC PULSE tone signal. The five second interval is adjustable by means of resistor 130. When transistor 128 is OFF, the receiver circuit is enabled and any detected signals are fed to point A and into BIFET OP AMP 140. The SYNC PULSE is also inverted using a NOR gate and passed through a CMOS SWITCH 134 to bit 5 of the EPSON PX-8 data buss.

As each participant unit transmits heart beat information to the main unit receiver, the signal is first buffered using OP AMP 140 and then passed through a FULL WAVE PEAK DETECTOR/THRESHOLD COMPARATOR 142 and to the input of the DTMF DECODER 144.

When a valid DTMF tone pair is detected by DECODER 144, its STD output goes high and the binary value of the tone pair is latched into the $D_0$ to $D_3$ output bus. Pin 8 of NOR GATE 150 is low and Pin 9 thereof is high. When the DTMF stops after 60 ms and the serial data starts, the first logic zero to be detected is the start bit which causes a zero at pin 9 of NOR GATE 150 and a positive spike to be generated at the trigger input of XR-2240 COUNTER 152. COUNTER 152 then starts counting at the rate of 1067 per second. The D output of the COUNTER clocks 4094 SHIFT REGISTER 154 which converts the 8 bit serial data from the participant unit into an 8 bit parallel byte. Once this conversion is finished, the reset input of the COUNTER 152 goes high and the 8 bit byte present in SHIFT REGISTER 154 is latched into its output bus. The reset line of the SHIFT REGISTER also serves as a busy strobe for the EPSON PX-8 computer.

In order to interface the digital outputs and inputs of the decoder circuitry to the EPSON PX-8 computer, the circuitry is multiplexed and addressed as ports on the PX-8 data bus. This is done using the 4051 8 channel CMOS SWITCH 156 and a 4066 4 channel CMOS SWITCH 158 for the SYNC, SERIAL DATA and STD signals. The MT8870 DECODER 144 and 4094 SHIFT REGISTER 154 already contain tri-state outputs which can be directly tied to the PX-8 computer data bus.

DUAL D-TYPE FLIP FLOP 160 and TRANSISTORS 162 and 164 activate RELAYS 166 and 168 which, in turn, control the power supply to the audio amplifier and the threshold alarm, respectively.

Figure 6:
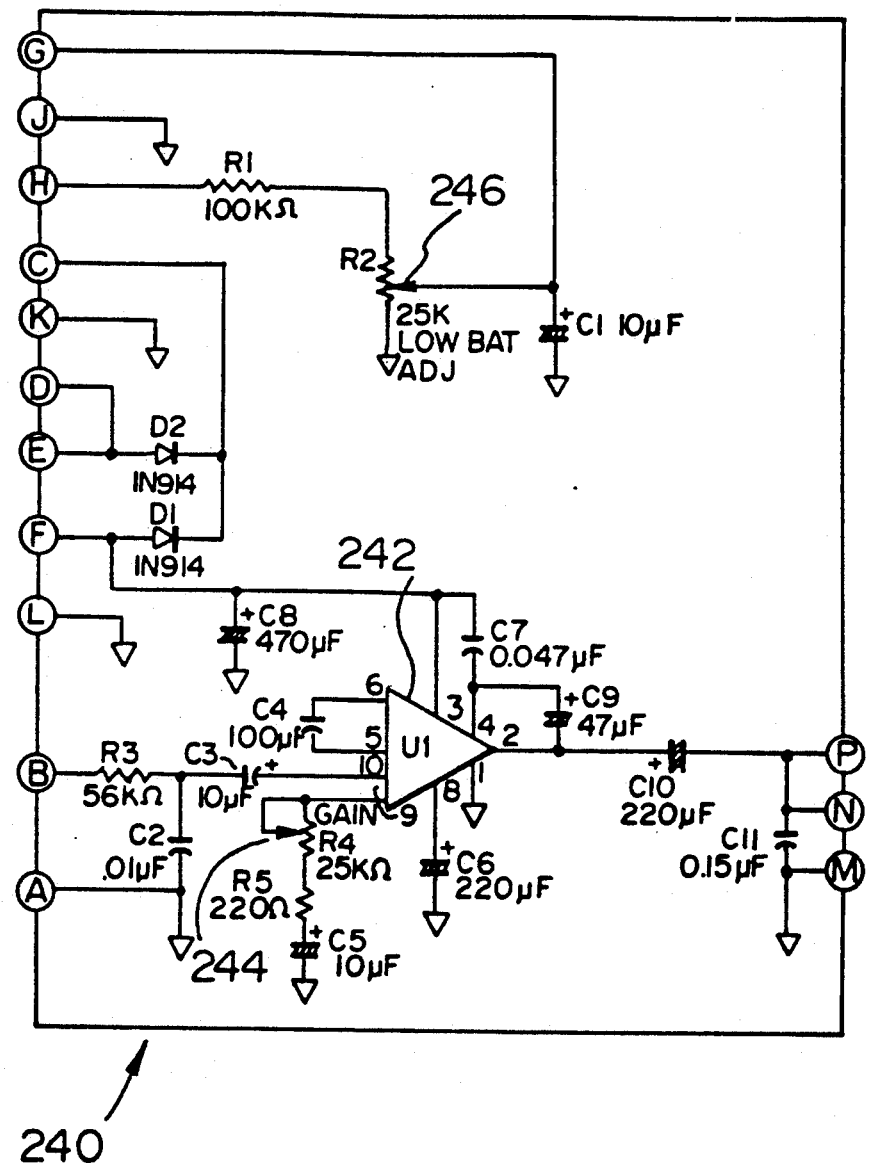
FIG. 6 is an electrical circuit diagram illustrating a charging circuit housed in the carrying case for charging rechargeable batteries associated the remote subcircuits according to a preferred embodiment of the present invention.

With reference to FIG. 6, charging circuit 170 consists of an adjustable voltage regulator 172 and a series pass transistor 174. This forms a fixed voltage, current limited charger for the Gel-Cell rechargeable 12 volt battery which provides power to the decoding circuitry. The 16 participant unit batteries are charged using diodes 181-196 and resistors 201-216. This provides taper current charging to each participant unit battery through the mounted plugs and unit jacks.

The input voltage for the charging circuitry is from the 28 volt center tapped transformer 108. This voltage is rectified using diodes 220 and 222 and filtered using capacitor 224. TRANSISTORS 226, 228 and 230 form a power switch to connect the Gel-Cell battery to the main unit circuitry. When the PX-8 is turned ON, transistor 230 is activated and a regulated 9 volts is applied to the main unit circuitry. All voltage sensitive components are powered by a 5.1 volt ZENER DIODE 232 regulated supply to reduce oscillator drift with battery decay.

FIG. 6 illustrates the amplifier circuit board 240. It includes a 4.5 watt AMPLIFIER 242 and circuitry for the audible alarm and a low battery indicator. Resistor 244 is provided to adjust the gain of the audio amplifier while resistor 246 scales the main battery voltage to a suitable level for a computer analog-to-digital converter.

OPERATION

Figure 8A:
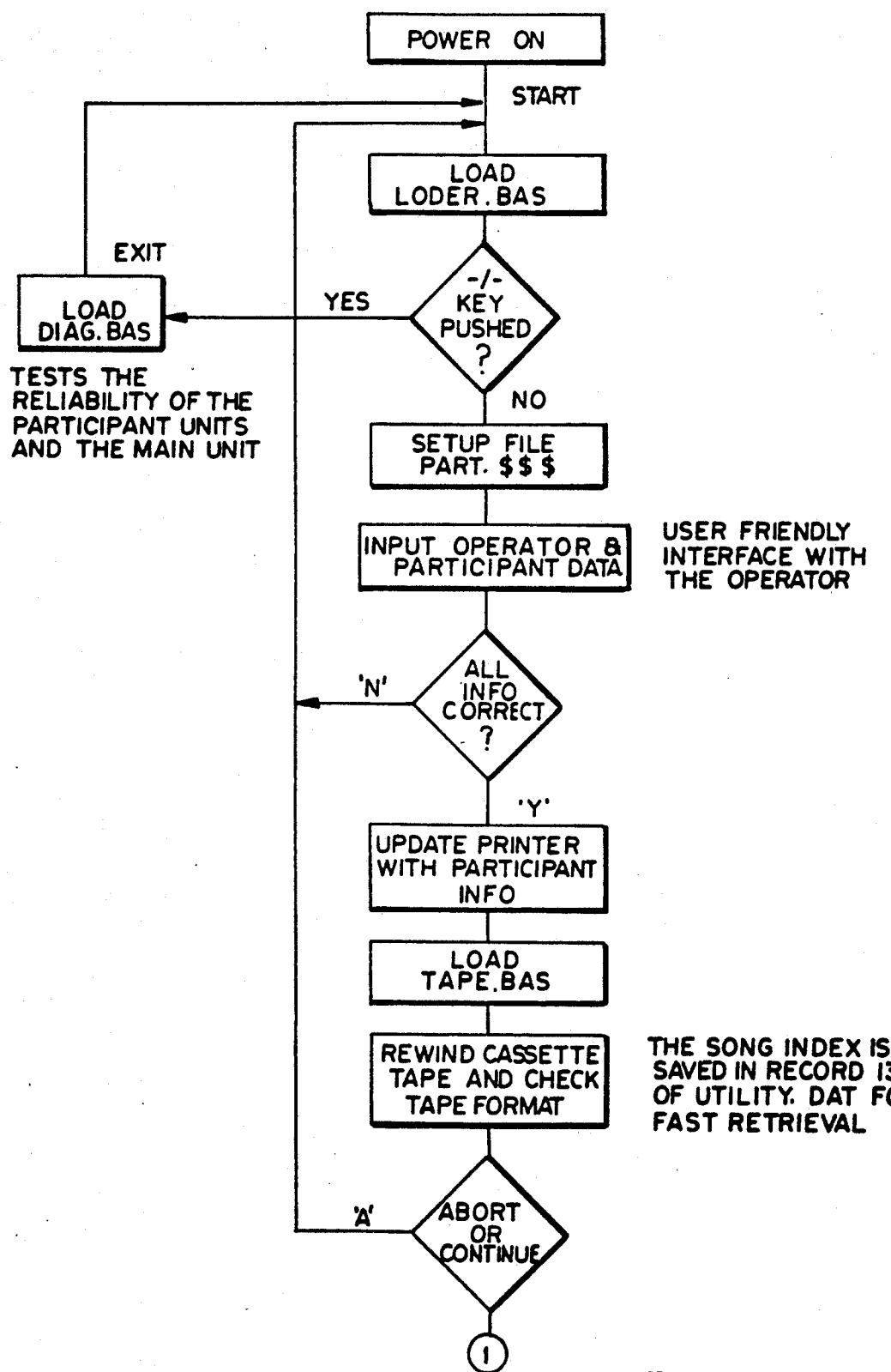
FIGS. 8a and 8b are a flowchart illustrating the fundamental mode of operation of the preferred embodiment of the present invention.
Figure 8B:
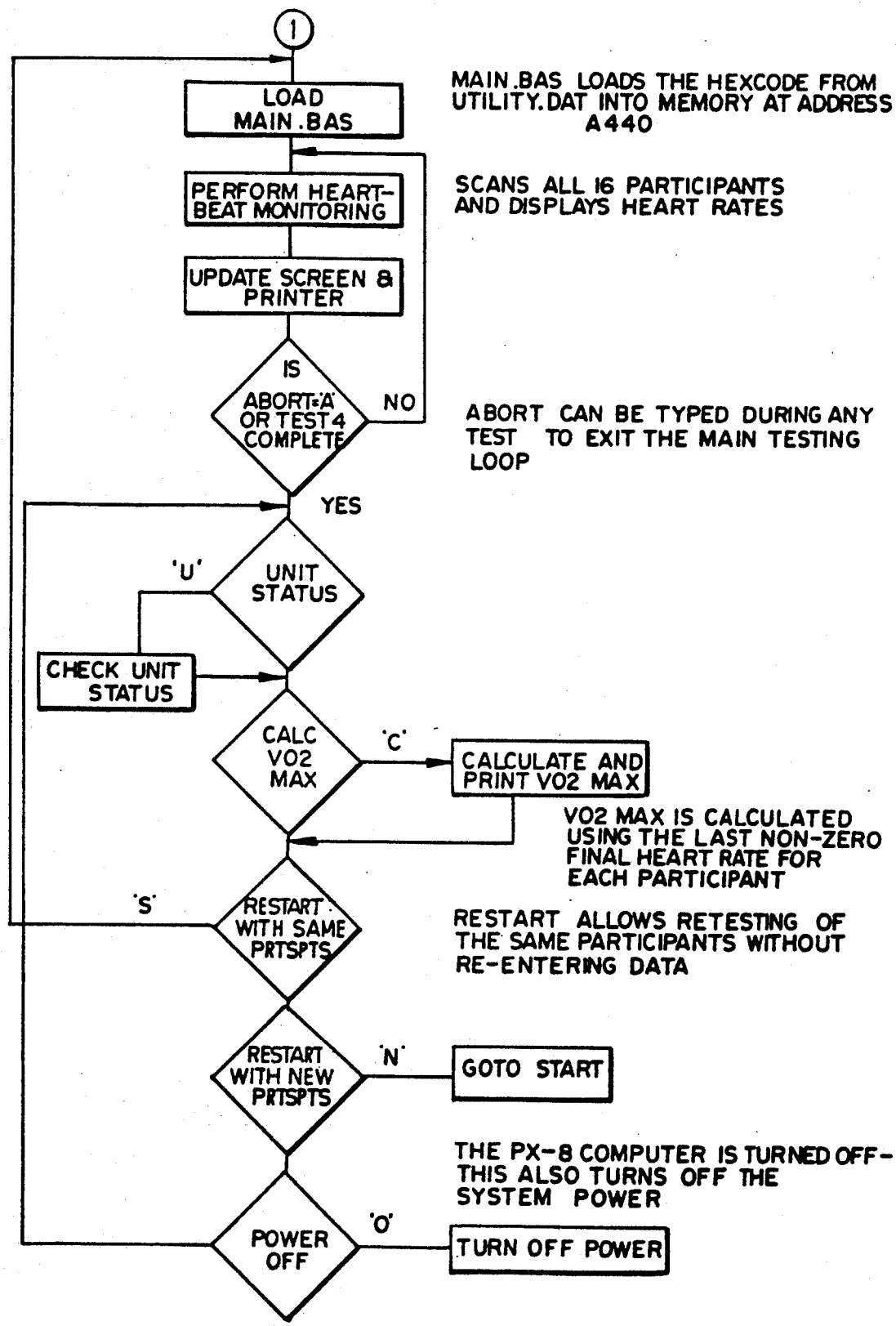

With reference to FIGS. 7 and 8, once the equipment has been arranged as shown in FIG. 1 and the computer has been turned ON, the screen illustrated in FIG. 7a will appear on the display terminal and, following about a one second delay, will be replaced by the screen illustrated in FIG. 7b. This screen requires the operator to enter his or her name and rank, the date and time. The <RETURN> key on the keyboard is depressed once this information has been entered, the computer will beep and the screen illustrated in FIG. 7c will appear. This screen requires the operator to enter the AGE GROUP of the participants or subjects, the number, which may range from 1 to 16, of subjects which will participate in the test and the sex of the subjects. Once this information has been entered and the <RETURN> key has been depressed, the computer will beep and the screen illustrated in FIG. 7d will appear.

This screen requires entry of the first subject's name, rank, age and weight. The computer will not accept a latter in the age or weight field and will beep and reject any age which does not fall within the age group previously specified in the screen illustrated in FIG. 7c. Once all of the information for the first participant has been entered, the <RETURN> key is depressed and a new blank screen will appear requiring information for the second subject.

This procedure continues until the relevant information for all subjects has been entered. At that point, the screen illustrated in FIG. 7e will appear. This screen displays the participant information in groups of four and allows the operator to review the information. Errors can be corrected by pressing the <C> key which will cause the screen illustrated in FIG. 7f to appear and allow modification of participant information. From the screen illustrated in FIG. 7e, the next group can be displayed by depressing the <space bar> on the computer keyboard. When the operator is satisfied that all information is correct, the <P> key is depressed and the screen illustrated in FIG. 7g appears.

If all data is correct, the operator turns the printer ON and depresses the <Y> key. The printer prints the operator's name, rank, the time and date and all of the participant data so as to provide a permanent record.

When the printing has stopped, the screen illustrated in FIG. 7h will appear and require the operator to enter the appropriate test music micro-cassette into the tape cassette player. The <RETURN> key is depressed when this has been completed. This will cause the tape to rewind and the screen illustrated in FIG. 7i to appear. At this time, the operator hands out the EXERSENTRY sensors and participant units described earlier.

After a short while, the printer will print system information and the screen which appears in FIG. 7j will appear on the display terminal. To ensure that all remote units are functioning properly, the operator may depress the <U> key to see the UNIT STATUS screen illustrated in FIG. 7k. The "HB or STAT" line will display either the subjects' heart beats or, if a unit is not being used, the word "OFF" will appear adjacent the remote unit number. The screen illustrated in FIG. 7k shows that only remote unit 1 is being used; the rest are "OFF". The "BATTERY" line displays indicates the condition of each of the remote units' battery. All units in use should have an "OK" notation indicating that their respective batteries are fully charged. The main battery voltage is indicated in the lower left hand corner of the screen and should be greater than 11 volts during normal operation for the circuitry described earlier and illustrated in the drawings. The operator returns to the screen illustrated in FIG. 7j by depressing the <E> key.

The operator may give a demonstration of the STEP TEST music by depressing the <D> key and causing the music for the first test will be played. The volume may be altered by adjusting the volume control knob located between the computer and printer behind the screen. When everyone is ready for the first test, the operator depresses the <F> key to stop the DEMO music. "PLEASE WAIT" will be displayed on the screen while the tape is rewound to the starting position.

The operator depresses the <RETURN> key to start the test causing the screen illustrated in FIG. 7l to appear on the display terminal. As the test progresses, the display and printer will be updated with the current participant heart rates. If at any time during the test, the heart of a participant exceeds the heart rate threshold of 174, a "+" will appear in front of the participant's heart rate and, if the same participant's heart rate exceeds the threshold twice during the test, an alarm will sound to alert the operator. The operator may remove the participant if the participant shows signs of fatigue. The operator depresses the <B> key to silence the alarm and the display will indicate that the BUZZER is turned OFF. It will be noted that the buzzer resets to the ON position at the beginning of each new test.

Two other characters may appear in front of the participants' heart rates. An "A" indicates that the heart rate shown was averaged because of faulty data transmission. These readings are accurate but if they appear often, the subject's EXERSENTRY must be checked to ensure that the chest electrode are making proper contact with the subject's skin. A "B" indicates that the transmission is bad.

When the music stops at the end of a test, the subjects should remain motionless until the music starts for the next test. The display will indicate the final heart rates for the participants. The operator reviews the data and decides whether participants whose heart rates exceed the threshold should continue. The operator depresses the <RETURN> key to continue with the next test.

The operator may abort the test by depressing the <A> key which will cause the screen illustrated in FIG. 7m to appear. This screen will also appear at the conclusion of the fourth and last test. The screen is self-explanatory. However, it will be noted that to determine the VO2 MAX, the final test results, the operator depresses the <C> key which causes the computer to do the calculations and the printer to print the results and the last completed test for each participant. Thereafter, the operator may select one of the other options shown on the screen.

The embodiments of the invention in which an exclusive property or privilege is claimed are defined as follows:

1. An apparatus for simultaneously monitoring the heart rate of each of a plurality of subjects, comprising:
    a main circuit having:
        means for transmitting a predetermined signal of predetermined frequency and duration and at predetermined time intervals to cause each of a plurality of remote subcircuits to transmit subcircuit identity data and heart rate data in predetermined timed sequence;
        means for receiving remote subcircuit transmissions and producing an output representative of the heart rate of a subject;
    a plurality of remote subcircuits, each said remote subcircuit having:
        pulse monitoring means adapted to be secured to a subject for detecting and producing an output in response to a heart beat;
        means for detecting said pulse monitoring means output and determining the number of said outputs which occur within a predetermined time interval;
        means responsive to said main circuit predetermined signal for transmitting to said main circuit a signal representative of subcircuit identity data and said number of said detected heart beats.

2. A heart rate monitoring apparatus as defined in claim 1, including computing means to monitor all system functions, a display terminal for displaying outputs from said computing means and printer means for recording outputs from said computing means.

3. A heart rate monitoring apparatus as defined in claim 2, further including a tape cassette player adapted to be controlled by said computing means.

4. A heart rate monitoring apparatus as defined in claim 3, further including a carrying case for said main circuit, said computing means, said display terminal, said printer means and said tape cassette player.

5. A heart rate monitoring apparatus as defined in claim 4, said carrying case further including a tray for storing each said remote subcircuits.

6. A heart rate monitoring apparatus as defined in claim 5, each said remote subcircuits including a rechargeable battery and said carrying case including charging means for charging said rechargeable battery of each said remote subcircuit when stored in said carrying case.

7. A heart rate monitoring apparatus as defined in claim 4, further including speaker means adapted to be connected to the audio output of said tape cassette player and said carrying case including storage compartments for said speaker means.

8. A heart rate monitoring apparatus as defined in claim 1, said main circuit means further including means for generating said predetermined signal and applying said signal to said transmitting means and means for activating said transmitting means at predetermined time intervals.

9. A heart rate monitoring apparatus as defined in claim 8, said activating means including timer means for producing a sync pulse of predetermined duration and a transistor responsive to said sync pulse.

10. A heart rate monitoring apparatus as defined in claim 8, said generating means and said activating means including timer means for producing a sync pulse of predetermined duration.

11. A heart rate monitoring apparatus as defined in claim 10, said predetermined time interval being five seconds.

12. A heart rate monitoring apparatus as defined in claim 8, said predetermined frequency being 2600 hz and said duration being 120 ms.

13. A heart rate monitoring apparatus as defined in claim 1, further including means for decoding the signal received from each said remote subcircuits and for transmitting decoded signals to a computing means adapted to determine the heart rate count of the person connected to said pulse monitoring means and whether said count exceeds a predetermined threshold level.

14. A heart rate monitoring apparatus as defined in claim 13, said decoding means further including:
    a buffer for receiving said transmitted signal;
    a full wave peak detector/threshold comparator;
    a Dual Tone MultiFrequency decoder for detecting a valid dual tone multifrequency tone pair and latching onto the binary value of the tone pair;
    timer means for producing a clock signal;
    a shift register for receiving serial data in said transmitting signal and responsive to said clock signal for converting said serial data to parallel data; and
    interface means for inputting said parallel data into said computing means.

15. A heart rate monitoring apparatus as defined in claim 1, said transmitting means being an FM transceiver.

16. A heart rate monitoring apparatus as defined in claim 1, said representative signal being a dual tone multifrequency signal wherein one portion of said signal being at one frequency and including serial data representative of the identity of the remote subcircuit and another portion of said signal being at another frequency and including serial data representative of the number of tone bursts detected during a predetermined time interval.

17. A heart rate monitoring apparatus as defined in claim 1, each said remote subcircuit further including:
- an FM TRANSCEIVER having an FM RECEIVER having a receiver input and a receiver output and an FM TRANSMITTER having a transmitter input and a transmitter output;
- a first TONE DECODER adapted to lock onto the output of said pulse monitoring means and produce a predetermined output signal when so locked;
- a RIPPLE COUNTER adapted to increment its output in response to each said predetermined TONE DECODER output;
- an SHIFT REGISTER connected to and adapted to receive the output of said RIPPLE COUNTER;
- a second TONE DECODER connected to said RECEIVER OUTPUT and producing a SYNC PULSE in response to said predetermined signal transmitted by the main circuit;
- an OSCILLATOR for producing a clock signal;
- a BINARY COUNTER having a clock, a count output, a shift register clock output, an output connected to a RECEIVER input of a transceiver circuit for activating the receiver thereof and monitoring main circuit transmissions and a DTMF output, said BINARY COUNTER being adapted to receive said clock signal from said OSCILLATOR, said SYNC PULSE from said second TONE DECODER, said BINARY COUNTER being inoperative until reset by said SYNC PULSE and, when reset, said BINARY COUNTER being operative to enable said clock, produce a count output, turn OFF said receiver, reset said RIPPLE COUNTER, provide a clock signal to said SHIFT REGISTER and provide, during a first time interval, a first output to a DTMF GENERATOR indicative of a first type of signal to be transmitted and, during a second, immediately following time interval, a second output to said DTMF GENERATOR indicative of a second type of signal to be transmitted;
- a DIP SWITCH adapted to provide a subject unit ID CODE;
- a MAGNITUDE DETECTOR adapted to receive the count output of said BINARY COUNTER and said ID CODE and produce a CE output when said count output matches said ID CODE; and
- a DUAL TONE MULTIFREQUENCY (DTMF) GENERATOR adapted to receive said CE output from said MAGNITUDE DETECTOR, said first and second outputs of said BINARY COUNTER, and said ID CODE from said DIP SWITCH, whereby upon receipt of said CE output and said BINARY COUNTER first output, said GENERATOR being adapted to enable said transmitter and apply to the input thereof a first signal of predetermined frequency and duration representing at least the identity of said remote subcircuit, upon receipt of said BINARY COUNTER second output, said GENERATOR transmitting an output signal of a different frequency and causing said SHIFT REGISTER to transmit its data to said transmitter input.

18. A heart rate monitoring apparatus, comprising:
a main circuit having:
- a main circuit TRANSCEIVER including a FM RECEIVER having a receiver input and a receiver output and an FM TRANSMITTER having a transmitter input and a transmitter output;
- means for generating and applying to said TRANSMITTER input a predetermined signal of predetermined frequency and duration and at predetermined time intervals, said signal being operative to cause a plurality of remote subcircuits to transmit in predetermined timed sequence identity and heart rate data;
- means for activating said TRANSMITTER at predetermined time intervals including a timer means for producing a sync pulse of predetermined duration and a transistor responsive to said sync pulse for enabling said TRANSMITTER;
- means for decoding the signal received from each said remote subcircuits and producing a decoded signal; and
- computing means adapted to receive said decoded signal from said shift register and provide at least the heart rate count of the person connected to said pulse monitoring means;

a plurality of remote subcircuits, each said remote subcircuit having:
- a subcircuit FM TRANSCEIVER including a RECEIVER having a receiver input and a receiver output and a TRANSMITTER having a transmitter input and a transmitter output;
- pulse monitoring means adapted to be secured to a subject for detecting the peak in said subject's EKG waveform and, in response to each detected peak, produce a tone burst signal at a predetermined frequency and duration;
- means for storing the number of said tone burst signals detected during a predetermined time interval; and
- means responsive to receipt of said predetermined signal at said receiver input for applying to said transmitter input and transmitting from said transmitter output to said main circuit means a signal representative of the identity of said remote subcircuit and said number of said tone burst signals.

19. A heart rate monitoring apparatus as defined in claim 18, said decoding means including:
- a BUFFER for receiving said transmitting signal;
- a FULL WAVE PEAK DETECTOR/THRESHOLD COMPARATOR;
- a DUAL TONE MULTIFREQUENCY DECODER for detecting a valid dual tone multifrequency tone pair and latching onto the binary value of the tone pair;
- timer means for producing a clock signal; and
- a SHIFT REGISTER for receiving serial data in said transmitting signal and responsive to said clock signal for converting said serial data to parallel data.

20. A heart rate monitoring apparatus as defined in claim 19, each said remote subcircuit further including:
- a first TONE DECODER adapted to lock onto the output of said pulse monitoring means and produce a predetermined output signal when so locked;
- a RIPPLE COUNTER adapted to increment its output in response to each said predetermined TONE DECODER output;
- an SHIFT REGISTER connected to and adapted to receive the output of said RIPPLE COUNTER;
- a second TONE DECODER connected to said RECEIVER OUTPUT and producing a SYNC PULSE in response to said predetermined signal transmitted by the main circuit;
- an OSCILLATOR for producing a clock signal;
- a BINARY COUNTER having a clock, a count output, a shift register clock output, an output connected to a RECEIVER input of a transceiver circuit for activating the receiver thereof and monitoring main circuit transmissions and a DTMF output, said BINARY COUNTER being adapted to receive said clock signal from said OSCILLATOR, said SYNC PULSE from said second TONE DECODER, said BINARY COUNTER being inoperative until reset by said SYNC PULSE and, when reset, said BINARY COUNTER being operative to enable said clock, produce a count output, turn OFF said receiver, reset said RIPPLE COUNTER, provide a clock signal to said SHIFT REGISTER and provide, during a first time interval, a first output to a DTMF GENERATOR indicative of a first type of signal to be transmitted and, during a second, immediately following time interval, a second output to said DTMF GENERATOR indicative of a second type of signal to be transmitted;
- a DIP SWITCH adapted to provide a subject unit ID CODE;
- a MAGNITUDE DETECTOR adapted to receive the count output of said BINARY COUNTER and said ID code and produce a CE output when said count output matches said ID CODE; and
- a DUAL TONE MULTIFREQUENCY (DTMF) GENERATOR adapted to receive said CE output from said MAGNITUDE DETECTOR, said first and second outputs of said BINARY COUNTER, and said ID CODE from said DIP SWITCH, whereby upon receipt of said CE output and said BINARY COUNTER first output, said GENERATOR being adapted to enable said transmitter and apply to the input thereof a first signal of predetermined frequency and duration representing at least the identity of said remote subcircuit, upon receipt of said BINARY COUNTER second output, said GENERATOR transmitting an output signal of a different frequency and causing said SHIFT REGISTER to transmit its data to said transmitter input.

21. A heart rate monitoring apparatus as defined in claim 20, said computing means including a display terminal for displaying outputs from said computing means, a keyboard for entering data into said computing means, and printer means for recording outputs from said computing means.

22. A heart rate monitoring apparatus as defined in claim 21, further including a tape cassette player adapted to be controlled by said computing means.

23. A heart rate monitoring apparatus as defined in claim 22, further including a carrying case for main circuit means, said computing means, said display terminal, said printer means and said tape cassette player.

24. A heart rate monitoring apparatus as defined in claim 23, said carrying case further including a tray for storing each said remote subcircuits.

25. A heart rate monitoring apparatus as defined in claim 24, each said remote subcircuits including a rechargeable battery and said carrying case including charging means for charging said rechargeable battery of each said remote subcircuit.

26. A heart rate monitoring apparatus as defined in claim 25, further including speaker means adapted to be connected to the audio output of said tape cassette player and said carrying case including storage compartments for said speaker means.

27. A heart rate monitoring apparatus as defined in claim 18, each said remote subcircuit further including:
- a first TONE DECODER adapted to lock onto the output of said pulse monitoring means and produce a predetermined output signal when so locked;
- a RIPPLE COUNTER adapted to increment its output in response to each said predetermined TONE DECODER output;
- an SHIFT REGISTER connected to and adapted to receive the output of said RIPPLE COUNTER;
- a second TONE DECODER connected to said RECEIVER OUTPUT and producing a SYNC PULSE in response to said predetermined signal transmitted by the main circuit;
- an OSCILLATOR for producing a clock signal;
- a BINARY COUNTER having a clock, a count output, a shift register clock output, an output connected to a RECEIVER input of a transceiver circuit for activating the receiver thereof and monitoring main circuit transmissions and a DTMF output, said BINARY COUNTER being adapted to receive said clock signal from said OSCILLATOR, said SYNC PULSE from said second TONE DECODER, said BINARY COUNTER being inoperative until reset by said SYNC PULSE and, when reset, said BINARY COUNTER being operative to enable said clock, produce a count output, turn OFF said receiver, reset said RIPPLE COUNTER, provide a clock signal to said SHIFT REGISTER and provide, during a first time interval, a first output to a DTMF GENERATOR indicative of a first type of signal to be transmitted and, during a second, immediately following time interval, a second output to said DTMF GENERATOR indicative of a second type of signal to be transmitted;
- a DIP SWITCH adapted to provide a subject unit ID CODE;
- a MAGNITUDE DETECTOR adapted to receive the count output of said BINARY COUNTER and said ID code and produce a CE output when said count output matches said ID CODE; and
- a DUAL TONE MULTIFREQUENCY (DTMF) GENERATOR adapted to receive said CE output from said MAGNITUDE DETECTOR, said first and second outputs of said BINARY COUNTER, and said ID CODE from said DIP SWITCH, whereby upon receipt of said CE output and said BINARY COUNTER first output, said GENERATOR being adapted to enable said transmitter and apply to the input thereof a first signal of predetermined frequency and duration representing at least the identity of said remote subcircuit, upon receipt of said BINARY COUNTER second output, said GENERATOR transmitting an output signal of a different frequency and causing said SHIFT REGISTER to transmit its data to said transmitter input.

28. A heart rate monitoring apparatus as defined in claim 18, further including an audible alarm, said computing means being further adapted to activate said alarm if the heart rate count of a subject exceeds a predetermined threshold level.

29. A kit for use in simultaneously monitoring the heart rate of each of a plurality of subjects, said kit comprising:

a carrying case;

a microcomputer, including a video display screen and keyboard, mounted in said case;

a printer mounted in said case and adapted to be connected to said microcomputer;

a tape cassette player mounted in said case and adapted to be connected to and controlled by said microcomputer;

audio speaker means removably mounted in said case and adapted to be connected to said tape player;

a primary circuit means mounted within said case and electrically connected to said microcomputer and including transmitter and receiver means for receiving and transmitting radio signals, encoding circuitry for generating and transmitting a single predetermined radio signal at predetermined intervals and digital decoding circuitry for decoding received digital signals and imputing said signals into said microcomputer; and a plurality of participant units adapted to be stored in said case and being removable therefrom for attachment to a test participant, each said participant unit being adapted to be electrically connected to a participant pulse monitoring device and including:

secondary circuit means including circuit means adapted to receive the output of said pulse monitoring device for detecting and storing the number of participant heart beats occurring within a predetermined time interval and for encoding data for transmission to said primary circuit means; and transmitter and receiver means for receiving said predetermined radio signal transmitted by said primary circuit means and transmitting encoded participant data thereto in a predetermined timed sequence in response to receiving said predetermined radio signal.

30. A kit as defined in claim 29, each said participant unit including a rechargeable battery and said primary circuit means including charging circuit means for selectively charging said batteries when said units are stored in said case. a

* * * * *